United States Patent [19]

Cambiaso et al.

[11] 4,184,849

[45] Jan. 22, 1980

[54] MIXED AGGLUTINATION

[75] Inventors: Cesar L. Cambiaso, Kraainem; Floris de Steenwinkel, Brussels; Adrian E. Leek, Diegem; Pierre L. Masson, Brussels, all of Belgium

[73] Assignee: Technicon Instruments Corporation, Tarrytown, N.Y.

[21] Appl. No.: 857,476

[22] Filed: Dec. 5, 1977

[51] Int. Cl.$^2$ .................. G01N 31/02; G01N 33/16
[52] U.S. Cl. .................. 23/230 B; 23/915; 435/7; 424/12
[58] Field of Search .................. 23/230 B; 424/1, 12; 195/103.5 A

[56] References Cited

U.S. PATENT DOCUMENTS

| 3,088,875 | 5/1963 | Fisk | 424/12 |
| 3,564,089 | 2/1971 | Kiddy | 424/12 X |
| 3,826,613 | 7/1974 | Parikh et al. | 23/230 B |
| 3,853,987 | 12/1974 | Dreyer | 23/230 B |
| 3,862,302 | 1/1975 | Price et al. | 424/12 |
| 3,862,303 | 1/1975 | Anderson | 424/12 |
| 3,873,683 | 3/1975 | Fishbein | 424/12 |
| 3,876,504 | 4/1975 | Koffler | 424/12 X |
| 3,925,541 | 12/1975 | Hirata | 424/12 |
| 3,981,982 | 9/1976 | Oslapas | 424/12 X |
| 4,031,117 | 6/1977 | Rao | 424/12 X |

FOREIGN PATENT DOCUMENTS 951242 7/1974 Canada ................ 424/12
2615092 10/1976 Fed. Rep. of Germany ........ 424/12

OTHER PUBLICATIONS

Chem. Abstract 68104u, vol. 80, 1974.
Chem. Abstract 107467, vol. 75, 1971.
Lalezari, pp. 778–792, Brit. J. of Medicine, vol. 24, (1973).
Singer et al., Am. J. of Medicine, pp. 888–892, Dec. 1956.
Ploty et al., Am. J. of Medicine, pp. 893–896, Dec. 1956.
Coombs et al., Progr. Allergy, vol. 13, pp. 174–272, (1969).

Primary Examiner—Michael S. Marcus
Attorney, Agent, or Firm—S. P. Tedesco; Robert S. Salzman

[57] ABSTRACT

The presence of antibodies (Ab) and antigens (Ag) in a liquid is detected by mixing the liquid with two different particulate reagents which mutually agglutinate but whose agglutination is inhibited by the particular Ab or Ag under assay. By detecting the extent of agglutination, the presence or absence of the Ab or Ag can be confirmed. By measuring the extent of agglutination or non-agglutination quantitatively, an amount of Ab or Ag can be determined. The particulate reagents preferably comprise latex.

17 Claims, No Drawings

MIXED AGGLUTINATION

This invention relates to the analysis of liquids, particularly but not exclusively biological fluids such as serum, for the presence therein of antigens or antibodies. In this specification, the symbols "Ag," "Ab" and "Ab:Ag" are used, respectively, for antigen(s) (by which term we include haptens and other substances which can be bound by antibodies or similar binding proteins), antibody(ies) (including similar binding proteins) and antibody:antigen complex(es).

It is well known that Ag will react with an appropriate Ab to form Ab:Ag and most immunoassay procedures make use of this reaction. It is further known to coat particulate materials such as polystyrene (generally referred to as latex) with an Ab or Ag, and then to expose the coated particles to a sample solution under test, to see whether and to what extent the particles become agglutinated. Agglutination indicates the presence in the sample of an Ab or Ag capable of reacting with two or more coated latex particles to cause agglutination.

Whilst the technique for observing agglutination of coated particles is in many respects satisfactory, there are problems in assaying small Ag, i.e. Ag whose molecular weight is less than about 4000. Such Ag are very small relative to the particulate materials used, so that discernible agglutination often does not occur or does not occur to any great extent. The technique is, therefore, not wholly reliable for the assay of small Ag.

We have now devised an improved technique for assaying Ab and Ag in a liquid (both to detect their presence and, if desired, to measure the quantity) which is particularly useful for assaying small Ag (or Ab) and can also be used for larger Ag (or Ab).

In one aspect, the invention provides a method of testing a liquid for the presence therein of a particular Ag or Ab, which comprises forming a mixture of the liquid with two different microscopic or sub-microscopic particulate reagents, which two reagents mutually agglutinate when incubated together, the particular Ag or Ab under assay inhibiting the mutual agglutination of the two reagents; and determining the presence or absence of the said particular Ag or Ab from the extent of agglutination or non-agglutination of the two particulate reagents.

In another aspect, the invention provides a method of quantitatively assaying a particular Ag or Ab in a liquid, which comprises (a) forming a mixture of:
  (i) a sample of the liquid containing the said particular Ag or Ab under assay,
  (ii) a first particulate reagent comprising solid particulate support material carrying a first substance, and
  (iii) a second particulate reagent comprising solid particulate support material carrying a second substance, the said first substance being capable of binding with the said second substance to cause the first and second reagents to agglutinate together, at least the first substance also being capable of binding with the particular Ag or Ab in the sample to inhibit the binding between said first substance and said second substance (b) incubating the mixture to allow the said Ag or Ab to bind with said first substance and to allow any of said first substance not bound to the said particular Ag or Ab to bind with said second substance and so cause agglutination of first and second reagents, and (c) measuring the extent of agglutination or non-agglutination of the said particulate reagents and thereby determining the amount of the said particular Ag or Ab present in the sample.

In accordance with the invention, two different particulate reagents are used simultaneously (in contrast to prior art procedures in which only one particulate reagent is used). These two reagents are such that they will agglutinate when mixed together but remain unagglutinated prior to mixing. For example, one particulate reagent may comprise an Ag or Ag-conjugate and the other an Ab which will bind with the Ag or Ag-conjugate. Upon mixing the two reagents, the Ab will bind with the Ag (or Ag-conjugate) to cause agglutination of the particles. At least one of the particulate reagents is so chosen, however, that it will also bind with the particular Ab or Ag under assay in the liquid. Binding of the particulate reagent with the free Ab or Ag under assay blocks the binding sites on the particulate reagent so that it is no longer able to bind and agglutinate with the other particulate reagent. The extent of agglutination in the mixture is thus reduced (over that amount which would occur in the absence of the particular Ag or Ab from the liquid) by an amount dependent on the amount of the particular Ag or Ab under assay in the liquid. By observing this phenomenon, the presence of the particular Ab or Ag can be confirmed, and by measuring the extent of agglutination or non-agglutination, the amount of the particular Ab or Ag can be determined. This is usually most conveniently effected by constructing a standard curve from results obtained using known concentrations of particular Ab or Ag under assay, and then using the curve to determine the (previously unknown) amount of Ab or Ag in a sample under test.

The method of the invention can, we believe, be used with any Ag and it does not require specific Ab on the particulate reagent since specificity may be introduced by the Ag-coated particulate reagent. Thus, for example, suppose the Ab coating on one particulate reagent was non-specific so that it could react with three different Ag and it was desired to assay a fluid sample for only one of these Ag (namely Ag'), then by using an Ag'-coated particulate reagent with the Ab-coated reagent, assay of Ag' can be effected. The technique may be used in the same manner for the detection and measurement of Ab in a sample.

The particulate reagents used in the method of the invention are of microscopic or sub-microscopic size, i.e. they will generally be smaller than 15 microns and most usually of the order of a few microns or sub-micron in size. Latex particles of such sizes are commercially available. It is known to bind Ab or Ag to microscopic particulate material such as latex. This is usually effected by providing a reactive coating on the particle, and then chemically linking or adsorbing the Ab or Ag thereon. It is also possible in certain circumstances to bind the Ab or Ag directly to the particle (with no intervening coating). Since the manner of preparation of the particulate reagents does not form part of the present invention and is well known in the art, no further description thereof will be given.

Among the Ag and Ab which can be bound to particulate materials (such as latex) for the purposes of this invention are, for example: as Ab, immunoglobulin G (IgG) from human, rabbit, goat and sheep serum, as well as their F (ab)$_2'$ fragments; rabbit IgM; as Ag, human IgM, human placental lactogen, human α-fetoprotein, human lactoferrin, human serum, albumen, human transferrin, human C-reactive protein and Fc fragment of human IgG; bovine IgG and serum albumin; horse ferritin; IgG's of human, mouse, rat and guinea pig, and the purified sub-classes 1, 2, 3 and 4 of human IgG. Also, we have bound thyroxine conjugates of human serum albumen, IgG and transferrin, bovine albumen and fibrinogen, and horse ferritin; also digoxin conjugates of human and bovine albumen and bovine IgG. Thyroxine may be bound directly to polystyrene latex particles which have reactive carboxyl groups on their surface.

It is preferred that the particle size of each particulate reagent be substantially uniform and, as will be described in more detail hereinafter, that the particle size of the first particulate reagent be different from (preferably at least twice that of) that of the second particulate reagent.

In carrying out the method of the invention to detect the presence of a particular Ag or Ab, it is merely necessary to establish whether any inhibition or agglutination has occurred. When there are relatively large quantities of Ag or Ab present in the sample under assay, it is possible to detect inhibition of agglutination by naked eye by observation through a microscope, the mixture being spread on a microscope slide. One particularly preferred test according to the invention is for detecting the presence of progesterone in cows' milk, wherein there is formed a mixture of the milk, a microscopic or sub-microscopic particulate reagent comprising progesterone or a progesterone conjugate, and a microscopic or sub-microscopic particulate reagent comprising an Ab which will bind both with progesterone and progesterone-conjugate. Examination of the mixture with the naked eye will usually reveal any inhibition of agglutination. It is also possible of course, in the tests to establish the presence or absence of inhibition of agglutination, to use one of the procedures to be hereinafter described in connection with quantitative assays.

In quantitative assays according to the invention, it is necessary to measure the extent of agglutination or non-agglutination of the particulate reagents. This may be effected in a variety of ways. For example, the agglutinated particles may be separated from the non-agglutinated particles, and the number of the latter then measured. Separation may be effected, for example, by filtering or centrifuging or by column chromatography. The number of unagglutinated particles may then be measured by, for example, counting or by using an identifying label (such as, for example, a radioactive atom) on the particulate reagent(s).

In general, however, we prefer to avoid a separation step since this is time-consuming and liable to introduce error. Instead, we prefer to make measurements on the reaction mixture to assess the extent of agglutination or non-agglutination. This may be conveniently effected by using selective counting techniques which are themselves known in the art. In this way, it is possible for example to count the number of particles in a given size range (particles of a size outside this range being ignored).

One known apparatus for effecting this is a Technicon Autocounter. In its basic form, this consists of an optical system such that light is passed through a flow-cell through which the diluted sample is pumped at right angles to the light beam. At the other end of the optical system is a photocell, and immediately behind the flowcell is a lens with a central black spot, to prevent light directly traversing the flowcell from reaching the photocell. When a particle is in the light-beam, a proportion of the incident light is scattered in such a way that it by-passes the black spot, and reaches the photocell. This registers an electronic impulse, and by summing these, a count of the particles in the sample may be made.

When using selective counting techniques, it is highly advantageous that the two particulate reagents be of a different size so that they can be distinguished by the counter. For such purposes, using particles of micron or sub-micron size, a difference in size of a factor of 2 is usually satisfactory. An illustration, merely by way of example, of operation of a method of the invention using selective counting is as follows. To the sample containing the Ag under assay are added the first and second particulate reagents, of sizes respectively 1 and 0.1 microns. The amount of first reagent added is known and is in excess of that required to bind with all the Ag in the sample. Part of the first reagent binds with the Ag, and is thereby inhibited from binding with the second reagent particles. Those first reagent particles, however, which have not bound with Ag in the sample, bind with the second particulate reagent to agglutinate. The mixture then contains (i) first reagent particles (unagglutinated) bound to Ag from the sample, (ii) excess second reagent particles (unagglutinated), and (iii) agglutinated particles. Since there is a difference in size between the unagglutinated first and second reagent particles, the number of unagglutinated first reagent particles (i) can be counted, and from the count (and standard results) the amount of Ag in the sample can be calculated.

Whilst it is highly preferred to proceed in this (or a similar) manner, it is not essential to use differently sized first and second reagents. Furthermore, it is possible to count the total number of particles, or the agglutinated particles in the mixture if desired, although the reproducability of results obtained by counting agglutinates is not always very satisfactory.

The method of the invention is particularly advantageous for assaying small Ag and Ab. In this connection, assays of steroids and drugs are among the most important.

In order that the invention may be more fully understood, the following Examples are given by way of illustration only.

EXAMPLE 1

This Example illustrates the assay of digoxin.

(a) Preparation of Ab-coated latex

Latex particles (0.09μ diameter, polystyrene, Dow Chemical Co.) as a 10% by weight suspension as supplied) was diluted 20-fold in dilute glycine-buffered saline (dGBS-20 mM glycine, 34 mM NaCl, pH 9) containing 0.2 mg/ml of the Rivanol-soluble fraction (prepared by the method of Stastny and Horejsi, Clin. Chim. Acta (1961), 6, 782) of sheep anti-digoxin serum, and incubated at room temperature for 30 minutes. 1/10th volume of 10 mg bovine serum albumin (bSA) per ml. dGBS was then added (to ensure that the latex was completely coated with protein), and after a further 30 minutes incubation, the coated latex was washed twice by centrifugation and resuspended in dGBS. Finally, the coated latex was resuspended as a 0.5% suspension in GBS (0.1 M glycine, 0.17 M NaCl, pH 9) containing 1 mg bSA/ml.

(b) Preparation of Ag-coated latex

The same procedure was followed as in (a) except that the latex used was of 1.1μ diameter and incubation was performed at an Ag-conjugate concentration of 4μg/ml, followed by the addition of 1/10 volume of 10 mg/ml transferrin. The Ag-conjugate was prepared by the oxidative coupling of digoxin and ethylene glycol followed by reductive coupling of this complex to the protein. 50 mg digoxin dissolved in 2 ml absolute alcohol was incubated for 25 minutes with 2 ml 0.1 M $NaIO_4$, then 60 μl of ethylene glycol was added for a further 5 minutes incubation. This reaction mixture was then added to a solution of 60 mg human transferrin in 2 ml water, brought to pH 9.5 by addition of 5% $Na_2CO_3$, and incubated for 45 minutes. 30 mg $NaBH_4$ freshly dissolved in 2 ml water was added and incubation was continued for 3 hours. At the end of this time, the pH of the reaction mixture was reduced to 6.5 by addition of 1 M HCOOH to destroy any unreacted $NaBH_4$, and after a further hour of incubation, 1 M $NH_4OH$ was added to raise the pH to 8.5, and the preparation was dialysed against running water for 2 days at 4° C. (all other operations were at room temperature).

(c) Assay

Sera used for the assay of digoxin were first heated with acid to reduce serum intereference. 25 μl of serum was heated to 56° C. for 10 minutes with 25 μl of 0.1 N HCl, then made alkaline by the addition of 10 μl 2 M $Na_2CO_3$. To these heated sera were added 25 μl of Ab-latex (diluted 1:10 with GBS containing 1 mg bSA/ml) and 25 μl of conjugate-latex (diluted 1:4 with GBS containing 1 mg human transferrin/ml). They were then incubated in vertically-positioned tubes agitated horizontally on a shaking incubator for 15 minutes at room temperature. At the end of this time, the tube contents were diluted with 5 ml GBS and after a further 20-fold dilution with GBS containing 0.01% Tween 20, passed through the flowcell of a Technicon Autocounter at 2 ml/min. The relative numbers of unagglutinated (monomer) latex particles in each sample were determined (as also may be the relative numbers of agglutinated particles) by selective optical counting. Table 1 lists the values obtained.

TABLE 1

| Inhibition of agglutination by digoxin in serum | |
|---|---|
| Digoxin concentration in serum (ng/ml) | Unagglutinated particles (as % of maximum) |
| 0 | 35 |
| 0.31 | 40 |
| 0.625 | 44 |
| 1.25 | 63 |
| 2.5 | 90 |
| 5.0 | 100 |

This method has also been successfully applied to the determination of dinitrophenol (DNP) using Ag conjugates of the hapten with bSA.

In the selective optical counting of particles, the amount of light scattered by a particle is dependent on the size of the particle; in turn, the electronic impulse generated in the photocell will be proportional to the size of the particle, and particles of different sizes may be counted separately. Table 2 illustrates the improvement in precision of determination (by providing a more extended range for the standard curve) that may be obtained by counting only unagglutinated particles (monomers) as opposed to counting all particles (total). The Table also illustrates the great increase in sensitivity that may be realized by calculating the ratio of unagglutinated to agglutinated particles (monomer/polymer ratio). By counting particles at all, an increase in sensitivity and precision may be realized by comparison with other methods of end-point determination.

TABLE 2

| Comparison of counting methods for latex immunoassay of hPL | | | |
|---|---|---|---|
| ngs hPL/ml | Total particles | Monomers | Monomer/polymer ratio |
| 0 | 100 | 100 | 100 |
| 2.5 | 100 | 100 | 81 |
| 5 | 100 | 98 | 68 |
| 10 | 97 | 94 | 55 |
| 20 | 90 | 82 | 30 |
| 40 | 78 | 62 | 13 |
| 60 | 67 | 46 | 8 |
| 80 | 57 | 36 | 6 |
| 100 | 50 | 30 | 5 |
| 160 | 40 | 22 | 5 |

Each value is expressed as a percentage of that obtained in the absence of hPL.

Table 3 shows a comparison of the results obtained by particle counting (monomers only) and turbidimetry (optical density at 400 nm) for a set of samples representing a standard curve for digoxin.

TABLE 3

| Comparison of counting vs. turbidimetry for latex immunoassay of digoxin | | |
|---|---|---|
| Digoxin concentration in serum (ng/ml) | Particle count (monomers) | Turbidity |
| 0 | 35 | 68 |
| 0.31 | 40 | 74 |
| 0.625 | 44 | 71 |
| 1.25 | 63 | 82 |
| 2.5 | 90 | 100 |
| 5.0 | 100 | 100 |

Each value is expressed as a percentage of that found in the presence of 5ng digoxin/ml (maximal inhibition).

EXAMPLE 2

This Example illustrates the assay of thyroxine.

(a) Preparation of thyroxine-coupled latex

Latex particles (0.857μ diameter, carboxylate-modified polystyrene, Dow Chemical Co.) as a 10% weight suspension (as supplied) was diluted 20-fold in phosphate buffered saline (PBS:50 mM in sodium phosphate, 0.17 M in NaCl, pH 6), centrifuged (at 12,000×g at 4° for 10 minutes), and resuspended in fresh PBS to a final weight suspension of 2%. A solution of 25 ug thyroxine and 50 ug 1-ethyl-3-(3-dimethylaminopropyl)-carbodiimide hydrochloride in 1 ml PBS was prepared at 0°, and 250 μl of the washed latex suspensions added. After incubation at 0° for 1 hour, 250 μl of 25% ethanolamine in PBS was added, and the incubation prolonged for 30 minutes. The latex was then washed twice by centrifugation and resuspension in fresh PBS (1 ml each time), and then dialysed for 16 hours at 4° against 1 l PBS. It was finally centrifuged and resuspended in 1 ml glycine-buffered saline containing 1% bovine albumen (bSA).

(b) Assay of thyroxine by mixed agglutination (i) Preparation of Ab-coated latex The method of this latex preparation was exactly the same as for the assay of digoxin (Example 1) except that the Ab was from rabbit anti-thyroxine ($T_4$) serum.

(ii) Preparation of Ag-coated latex

As above under (a).

(iii) Assay

Sera to be assayed for $T_4$ are first mixed with an equal volume of 1 mM 1-anilino-naphthalene-8-sulphonic acid in 75 mM sodium diethyl-barbiturate, pH 9.2. 50 μl of this diluted serum is then incubated with 25 μl 0.01% suspension of Ab-latex in GBS containing 1% bSA, and 25 μl 0.1% suspension of Ag-latex in the same buffer in the same way as for the assay of digoxin (Example 1). Table 4 illustrates typical results obtained using this system.

TABLE 4

| ng $T_4$/ml serum | Particle concentration (% maximum) |
|---|---|
| 0 | 48 |
| 10 | 51.5 |
| 50 | 59.5 |
| 200 | 89 |

The maximum value in this case was for the Ag-latex alone, all the above values being found in the presence of Ag-latex as well.

EXAMPLE 3

Example 1 was repeated using latex particles of the same (as opposed to different) size and the following results were obtained:

TABLE 5

| | Inhibition of agglutination by digoxin in serum | |
|---|---|---|
| | Unagglutinated Particles (as % of maximum) | |
| Digoxin concentration in serum (ng/ml) | Equal-sized latex | Different-sized latex |
| 0 | 60 | 21 |
| 1 | 78 | 30 |
| 4 | 95 | 76 |
| 10 | 100 | 100 |

What we claim is:

1. A method of assaying a sample containing a particular antigen or antibody constituent of interest, comprising the steps of:
   (a) forming a mixture of:
      (i) a first reagent bound with a first carrier;
      (ii) a second reagent bound with a second carrier of different size than said first carrier; and
      (iii) a sample containing said particular antigen or antibody constituent of interest;
   said first and second reagents tending to bind with each other to form a measurable reaction, and said particular constituent tending to bind with one of said reagents and preclude binding thereof with the other of said reagents;
   (b) incubating said mixture to effect binding between said first reagent, second reagent, and said constituent; and
   (c) measuring said reaction to determine the amount of said constituent in said sample.

2. The method according to claim 1, wherein said first and second carriers are different in size from each other by at least a factor of 2.

3. The method of assaying a sample in accordance with claim 1, wherein said first and second reagents respectively comprise an antigen and an antibody.

4. The method of assaying a sample in accordance with claim 1, wherein said first and second reagents respectively comprise an antigen-conjugate and an antibody.

5. A method of quantitatively assaying a particular antigen or antibody constituent in a liquid, which comprises:
   (a) forming a mixture of:
      (i) a sample of the liquid containing said particular antigen or antibody constituent under assay,
      (ii) a first reagent carried by a first particulate material, and
      (iii) a second reagent carried by a second particulate material of different size than said first particulate material, said first reagent being capable of binding with said second reagent to agglutinate said first and second particulate materials, at least the first reagent also being capable of binding with said particular constituent to inhibit the agglutination of said first and second particulate materials,
   (b) incubating the mixture to allow the said first reagent to bind, on a competitive basis, with said particular constituent and said second reagent, and
   (c) measuring the agglutination of said first and second particulate materials and thereby determining the amount of said particular constituent present in the sample.

6. A method according to claim 5, wherein said particular constituent is an antigen-type substance, and said first reagent is an antibody capable of binding with the antigen-type substance under assay and said second reagent is substantially the same antigen-type substance under assay which is capable of binding with said antibody.

7. A method according to claim 5, wherein said particular constituent is an antibody, and said first reagent is an antigen-type substance which is capable of binding with said antibody, and the second reagent is an antibody which is capable of binding with said antigen-type substance.

8. A method according to claim 5, wherein the respective particle size of each of said first and second particulate materials is substantially uniform.

9. A method according to claim 5, wherein at least one of said first or second particulate materials comprise latex.

10. A method of assaying a sample in accordance with claim 5, wherein said particular constituent under assay has a molecular weight of less than about 4000.

11. A method according to claim 6, wherein the particle size of said first particulate material is at least twice that of said second particulate material.

12. A method according to claim 11, wherein non-agglutinated first particulate materials in the mixture are selectively counted, and wherein in forming step (a) a known amount of first particulate materials are included in the mixture.

13. A method according to claim 5, wherein in measuring step (c) the extent of agglutination or non-agglutination is determined by counting agglutinated or non-agglutinated particulate materials.

14. A method according to claim 13, wherein the said count of said particulate materials is effected while they are present in the mixture.

15. A method according to claim 14, wherein non-agglutinated particulate materials are selectively counted by optical techniques.

16. A method according to claim 5, wherein, in measuring step (c) the agglutinated particulate materials are separated from the non-agglutinated particulate materials.

17. A method according to claim 16, wherein either said first particulate material or said second particulate material comprises an identifying label, and the extent of agglutination or non-agglutination is measured by assay of the label in the separated particles.

* * * * *